United States Patent
Yang (10) Patent No.: US 8,917,952 B2
(45) Date of Patent: Dec. 23, 2014

(54) PARALLEL IMAGE CONVOLUTION PROCESSING WITH SVD KERNEL DATA

(71) Applicant: Siemens Medical Solutions USA, Inc., Malvern, PA (US)

(72) Inventor: Faguo Yang, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 102 days.

(21) Appl. No.: 13/656,973

(22) Filed: Oct. 22, 2012

(65) Prior Publication Data

US 2014/0112596 A1    Apr. 24, 2014

(51) Int. Cl.
*G06K 9/64*    (2006.01)

(52) U.S. Cl.
USPC .......................................................... 382/279

(58) Field of Classification Search
USPC ........................ 382/279; 708/5, 315, 420, 813
See application file for complete search history.

(56) References Cited

U.S. PATENT DOCUMENTS

| | | | |
|---|---|---|---|
| 2009/0265404 A1* | 10/2009 | Tzeng | 708/208 |
| 2010/0251202 A1* | 9/2010 | Pierrat | 716/20 |
| 2010/0275178 A1* | 10/2010 | Wei | 716/56 |
| 2011/0085742 A1* | 4/2011 | Maurer | 382/260 |

OTHER PUBLICATIONS

Logic, Filtering with General 2D Kernels on LOGIC Devices, Inc.'s LF33xx Family of Devices, Apr. 25, 2001.*
Anderson et al., "PALLAS: Mapping Applications onto Manycore", Nov. 20, 2010, Springer, Chapter 4.*
W. H. Press, et al., Numerical Recipes: The Art of Scientific Computing, 3rd edition in C++, pp. 65-73 (2007).

* cited by examiner

*Primary Examiner* — Gregory F Cunningham
(74) *Attorney, Agent, or Firm* — Peter Kendall (57) ABSTRACT

A method of image processing includes receiving camera data representative of an object, implementing, with a processor, a convolution operation on the camera data to generate filtered data representative of the object, the convolution operation being configured with singular value decomposition (SVD) kernel data, and storing the filtered data in a memory. Implementing the convolution operation includes applying the SVD kernel data in parallel to a plurality of subsets of the camera data.

19 Claims, 4 Drawing Sheets

PARALLEL IMAGE CONVOLUTION PROCESSING WITH SVD KERNEL DATA

BACKGROUND

The present embodiments relate to image processing.

Image convolution is an operator used in digital image processing. Convolution is useful in, for example, image smoothing, edge detection, and correlation. Convolution may be represented as follows:

$$I_{out}(x, y) = \sum_{i=0}^{m} \sum_{j=0}^{n} I_{in}(x - n/2 + j, y - m/2 + i)K(i, j)$$

where $I_{in}$, $I_{out}$, and K are the input, convolved and kernel images, respectively, where m and n are the dimensions of the kernel image. The algorithm complexity of a direct implementation of the image convolution operator using a moving window is in the order of m×n×l×o, where l and o denote the dimensions of the input and convolved images. To reduce the computation cost, techniques such as multi-thread programming are employed, when the dimension of the image or the kernel is large.

For a separable kernel, defined as $K(x,y)=K_H(x)K_V(y)$, the two-dimensional image convolution operation may be efficiently implemented by applying the horizontal kernel, $K_H(x)$, and the vertical kernel, $K_V(y)$, separately. The one-dimensional horizontal kernel is applied to each row of the image and the result is a row-smoothed image $I_h$. The one-dimensional vertical kernel is then applied to each column of the row-smoothed image $I_h$. The algorithm complexity for separable kernels is thus simpler, and on the order of m×l×n+ m×n×o. The dimension complexity is greatly reduced relative to direct implementation using a moving two-dimensional window.

Unfortunately, not all two-dimensional kernels are separable.

BRIEF SUMMARY

By way of introduction, the preferred embodiments described below include methods, systems, instructions, and computer readable media for parallel processing of image convolution operations. In one embodiment, the image convolution operations are based on singular value decomposition (SVD) kernel data of a non-separable kernel.

In a first aspect, a method of image processing includes receiving camera data representative of an object, implementing, with a processor, a convolution operation on the camera data to generate filtered data representative of the object, the convolution operation being configured with singular value decomposition (SVD) kernel data, and storing the filtered data in a memory. Implementing the convolution operation includes applying the SVD kernel data in parallel to a plurality of subsets of the camera data.

In a second aspect, a non-transitory computer readable storage medium has stored therein data representing instructions executable by a programmed processor for image processing. The instructions include computer code to receive camera data representative of an object, apply singular value decomposition (SVD) kernel data to the camera data, the application convolving the camera data with a non-separable kernel represented by the SVD kernel data and generating filtered data representative of the object, and store the filtered data in a memory. The instructions to apply the SVD kernel data are configured to apply the SVD kernel data in parallel to multiple rows or multiple columns of the camera data.

In a third aspect, a system for image processing includes a first memory in which camera data representative of an object is stored, a processor configured to implement a convolution operation on the camera data to generate filtered data representative of the object, the convolution operation being configured with singular value decomposition (SVD) kernel data, and a second memory in communication with the processor to store the filtered data. The processor is further configured to apply the SVD kernel data in parallel to a plurality of subsets of the camera data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Systems, methods, and computer readable media are provided to smooth or otherwise filter images through image convolution implemented via parallel processing. Single-instruction, multiple-data (SIMD) and other parallel processing techniques may be used to process image data. The image convolution is based on singular value decomposition (SVD) of a non-separable smoothing or other kernel. With convolution tasks processed in parallel, the disclosed methods and systems may provide fast convolution of large images, notwithstanding the non-separable nature of the kernel. Convolving the image with SVD kernel data may be parallel processed via the SIMD techniques, such as Streaming SIMD Extension (SSE) techniques provided with processors available from Intel Corporation. The disclosed methods and systems may provide convolution performance about 10 times as fast as direct convolution using a moving window and multi-thread techniques, such as those supported by the Open Multiprocessing (OpenMP) application programming interface (API).

The parallel processing of the disclosed methods and systems may apply one instruction on multiple subsets of image or camera data. Each subset may correspond with a respective row or a respective column of the camera data. In some cases, the disclosed methods and systems use byte-aligned buffers for efficient processing of the camera data. For example, in embodiments using Intel Streaming SIMD (SSE) processing, the buffers may be configured such that the camera data and the SVD kernel data is 16 byte-aligned. Such byte alignment may support the SIMD processing as well as maintain cache efficiency during the numerous memory buffer copy and processing operations involved in the SIMD processing.

The method may include decomposition of the non-separable smoothing or other kernel into the set of separable two-dimensional kernels. In some cases, such decomposition may be implemented separately from the disclosed methods. For example, data indicative of the separable kernels may be predetermined. Such data may then retrieved or otherwise obtained during implementation of the disclosed methods.

The camera data may be representative of a variety of objects. One exemplary type of object is a collimator of an image acquisition system or scanner, such as a single photon emission computed tomography (SPECT) system. In some embodiments, a SPECT system may be configured in accordance with filtered data generated by the disclosed methods and systems. For example, the filtered data may provide an accurate representation of the positioning of the holes of the collimator. The kernel image in such cases may be similar to a single hole of the collimator (e.g., a hexagonal shaped image). The filtered data may be used during manufacturing, calibration, or other configuration of the SPECT system. Although described in connection with characterization of collimators, the disclosed methods, systems, and computer readable media are not limited to convolution of any particular type of image. The convolution processes may be applied to contexts other than the configuration of a scanner having a collimator. The disclosed methods, systems, and computer readable media are well suited for image convolution for a variety of purposes involving other types of large images.

Figure 1:
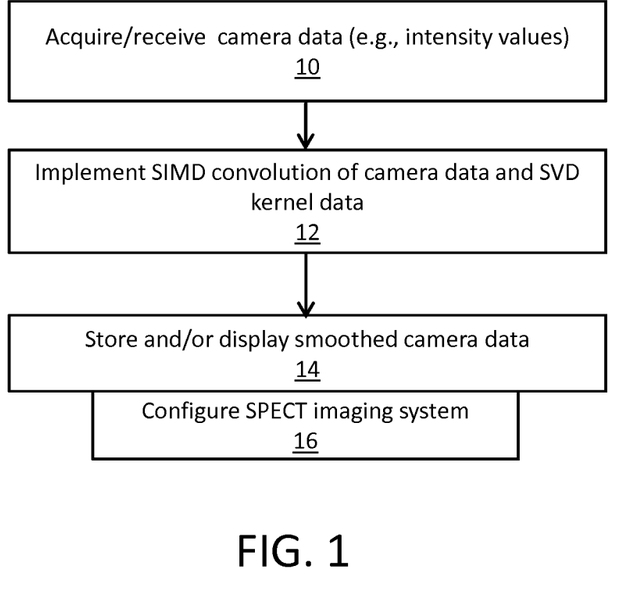
FIG. 1 is a flow chart diagram of one embodiment of an image convolution method with parallel processing based on singular value decomposition (SVD) kernel data.

FIG. 1 depicts an exemplary image convolution method in accordance with one embodiment. The method is directed to processing camera data indicative of an object. The camera data may include any type of image data. In some cases, the camera data is projection data. In other embodiments, the camera data is data in a spatial domain after reconstruction or tomography. The camera data may be acquired or generated via any type of camera or image acquisition system. Additional, fewer, or alternative acts may be included in the method. For example, the method may include the acquisition of the camera data. The camera data may thus be acquired or generated independently of, or in conjunction with, the implementation of the method.

The disclosed methods are well suited for convolution of large images. In one embodiment, the large image is representative of a collimator of a SPECT system. In one example, the camera data of the collimator image may have dimensions of about 3744×5616. The resolution or size of the image may vary. The collimator image may be convolved with an kernel image configured to clarify the positioning of the holes of the collimator. The camera data and disclosed methods may be used to configure the SPECT system by generating a vector map that characterizes the collimator. The vector map may specify center locations of the holes of the collimator, along with the angles or directions of the holes. The nature of the object may also vary. Any type of object may be represented by the camera data.

The camera data is obtained or otherwise received for image processing in an act 10. The camera data may be arranged in a two-dimensional array of pixels. Other formats or arrangements may be used. The camera data may be indicative of grayscale or other intensity values for each pixel or element in the array. The intensity values may be configured as float-type numbers. The camera data may thus be configured as pixel data. The camera data may be raw data (e.g., raw projection data) from an image acquisition system. In other cases, various types of preprocessing operations are implemented on raw camera data before receipt of the camera data.

The act 10 may include storing the camera data in a memory in preparation for processing. The memory may be a temporary storage location for the camera data. The memory need not be configured to accommodate the parallel processing of the disclosed methods. The configuration and other characteristics of the memory may thus vary.

Once the camera data is received, an image convolution operation is implemented in an act 12 to generate filtered data representative of the object. A kernel of the image convolution operation may be configured to smooth or otherwise filter the camera data. The image convolution operation is implemented via parallel processing of the camera data. In this example, the parallel processing of the camera data is configured for single-instruction, multiple-data (SIMD) processing. Further details regarding examples of SIMD processing are set forth below in connection with FIG. 2. The manner in which the camera data is parallel processed may vary.

The image convolution operation is configured with SVD kernel data. The SVD kernel data is representative of the kernel image to be convolved with the camera data. The kernel image may be non-separable, and thus not easily applied to the camera data. For example, the kernel image may have dimensions of about 25×25. In collimator examples, the kernel image may be similar to a single hole of the collimator (e.g., a hexagonal shaped hole), and thus not constitute a separable kernel. Separable kernel data is provided via decomposition of the kernel image as described below in connection with FIG. 2. The SVD kernel data is representative of a set of separable kernels. The SVD kernel data may be predetermined or generated before or during the act 12.

Each of the separable kernels is applied to the camera data via the parallel convolution processing of the disclosed methods. Implementing the convolution operation thus includes applying the SVD kernel data in parallel to a plurality of subsets of the camera data. For example, each subset may correspond with a respective row or a respective column of the camera data, as described below. For each separable kernel, SSE or other SIMD techniques may be used to process multiple rows (e.g., four rows) and/or multiple columns (e.g., four columns) together. A multi-threading technique, such as OpenMP, may be used to process multiple four-row and/or four-column groups in parallel. The procedure may then iterate over the other separable kernels serially.

The filtered data resulting from implementing the convolution operation is stored in a memory in act 14. The filtered data may be smoothed or processed to, for instance, reveal a pattern in the camera data. For example, the pattern may be the arrangement of holes of a collimator. The disclosed methods are not limited to any particular pattern, or to pattern recognition. The kernel image may be configured to provide other types of filtering. The nature of the smoothing or other filtering provided by the disclosed methods may vary.

The memory may be configured to support the parallel processing of the operation. For example, the memory may include a buffer configured to accommodate a number of subsets of the filtered data. The buffer may be used to accumulate the products of the application of the SVD kernel data to the camera data. Alternatively or additionally, the memory is configured to store the results of the image convolution after completion of the parallel processing.

The act 14 may alternatively or additionally include storage of the filtered data in an act 16 in connection with configuration of an image acquisition system. In some embodiments, a SPECT system may be configured in accordance with the filtered data. A collimator of the SPECT system may be characterized by a vector map computed or based on or otherwise including or involving the filtered data. The collimator acts as a front end of the SPECT system to limit the direction of the photons. The collimator may absorb those photons (e.g., gamma rays) not aligned with holes of the collimator. Only those photons aligned with the holes can reach a detector of the SPECT system.

The camera data may be used to accurately determine the positioning of the holes. The filtered data may be used during manufacturing, calibration, or other configuration of the SPECT system.

The construction of the collimator may vary. For example, the collimator may be configured with parallel holes or non-parallel holes. In non-parallel cases, the filtered data indicative of the locations of the holes may be combined with data indicative of the direction or angle of the holes. For example, the combination may be arranged in a vector map of the collimator that may, in turn, be used during image reconstruction from raw projection data generated by the SPECT system.

Additional steps may be included in the image convolution method of FIG. 1. For example, the implementation of the convolution in the act 12 may include the generation of one or more user prompts via a display or other user interface to allow an operator to select a kernel image for the image convolution operation. The user interface may also support initiation of the decomposition of the kernel image into a set of separable kernel images.

Figure 2:
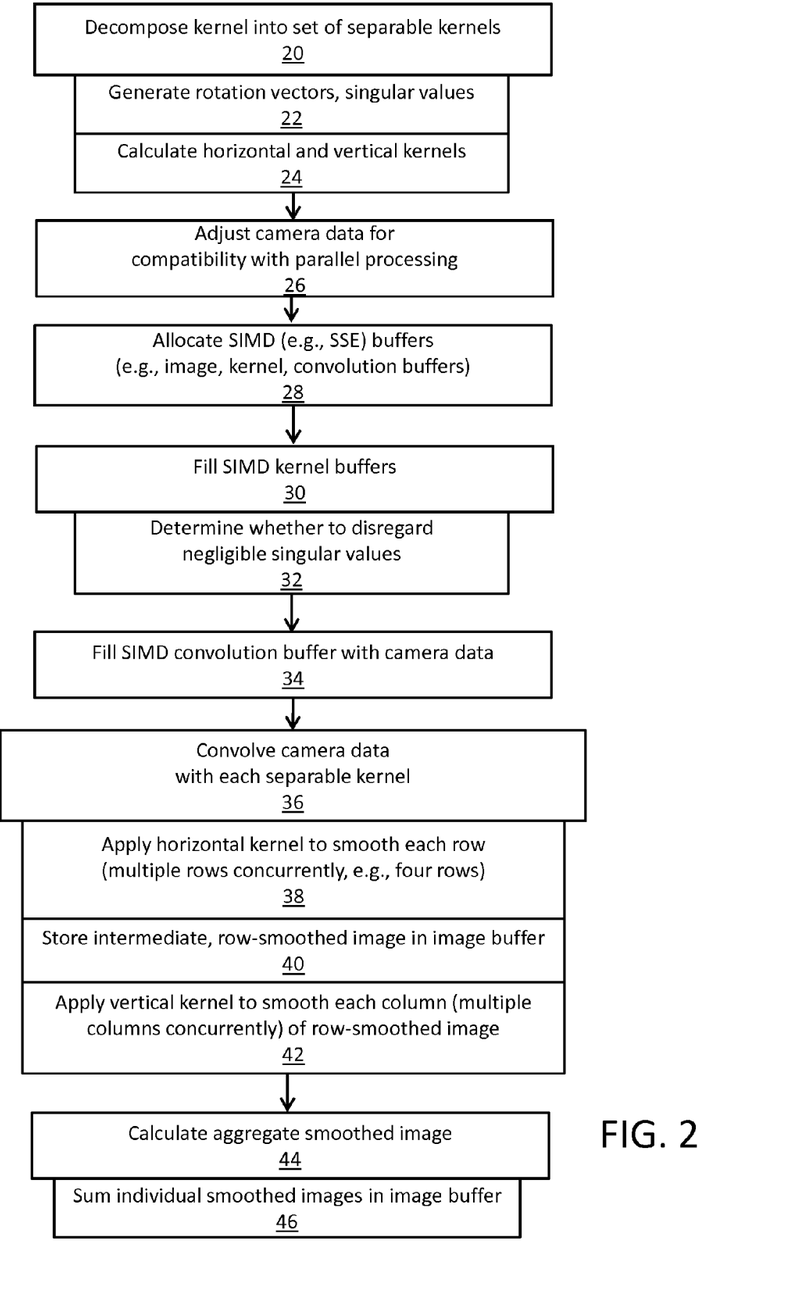
FIG. 2 is a flow chart diagram showing the image convolution method of FIG. 1 in greater detail and in accordance with one embodiment.

FIG. 2 depicts an example of an image convolution processing method in accordance with one embodiment. In this example, the method begins with decomposition of kernel image data into a set of separable kernels in an act 20. The kernel image data may be representative of a non-separable kernel image, such as the kernel images used during characterization of a collimator. Non-separable is used to describe a kernel that is not separable in simple row-column fashion. Instead, this type of non-separable kernel is converted to provide separation. Converting such kernel image data into the set of separable kernels may support the image convolution operation as follows.

The singular value decomposition of a non-separable kernel image $K_{mn}$, an m×n matrix with m≥n, may be expressed as a product of rotation vectors (or matrices) and a set of singular values, $K_{mn} = U_{mn} \Lambda_{nn} V_{nn}^T$, where $U_{mn}$ is a column-orthogonal matrix, $\Lambda_{nn}$ is a diagonal matrix with positive or zero singular values, and $V_{nn}$ is another orthogonal matrix. The decomposition may be written as follows:

$$K_{mn} = \begin{bmatrix} u_1 & u_2 & \cdots & u_n \end{bmatrix} \begin{bmatrix} \lambda_1 & & & \\ & \lambda_2 & & \\ & & \ddots & \\ & & & \lambda_n \end{bmatrix} \begin{bmatrix} v_1^T \\ v_2^T \\ \vdots \\ v_n^T \end{bmatrix}$$

where $u_i$ and $v_i$ are the column vectors of rotation matrices $U_{mn}$ and $V_{nn}$, respectively, and $\lambda_i$ is a non-negative singular value. With matrix multiplication, the kernel image $K_{mn}$ is rewritten as follows:

$$K_{mn} = \sum_{i=1}^{n} \lambda_i u_i v_i^T = \sum_{i=1}^{n} \sqrt{\lambda_i}\, u_i \left(\sqrt{\lambda_i}\, v_i\right)^T$$

which shows that the non-separable kernel image may be decomposed into a sum of a set of n separable or separated kernels denoted as $K_{mn}^i$ (i=1, ..., n). Combining the sum with the convolution operation expression, the convolution operation may be expressed as follows:

$$I_{out}(x, y) = \sum_{h=1}^{n} \left( \sum_{i=0}^{m} \sum_{j=0}^{n} I_{in}(x - N/2 + j, y - M/2 + i) K_{mn}^h(i, j) \right)$$

which shows that the image convolution operation may be implemented by first convolving an input image $I_{in}$ with each separable kernel $K_{mn}^i$ individually and denoting each individual smoothed image as $I_{out}^i$, and then summing or accumulating the individual smoothed images to obtain a final convolution image $I_{out}$.

As described below, for each separable kernel $K_{mn}^i = KH_m^i KV_n^i$, the parallel processing of the disclosed methods applies the horizontal kernel $KH_m^i$ on multiple (e.g., four) rows of the input image at the same time, and applies the vertical kernel $KV_n^i$ on multiple (e.g., four) columns at the same time.

The decomposition may include generation of the rotation vectors or matrices $U_{mn}$ and $V_{nn}$, and singular values in an act 22. Any one of a number of available algorithms or routines may be used to perform the SVD processing of the non-separable kernel image to generate the rotation vectors and the singular values.

In this embodiment, the SVD kernel data to be used in the convolution operation is generated in an act 24 by calculating horizontal and vertical kernel data for the set of separable kernels. Based on the above formula for $K_{mn}$, each column vector $u_i$ of $U_{mn}$ multiplied by $\sqrt{\lambda_i}$ is a horizontal one-dimensional kernel, and the corresponding vertical one-dimensional kernel is the column vector $v_i$ of $V_{nn}$ multiplied by $\sqrt{\lambda_i}$. Such horizontal and vertical kernel data may be calculated after performing the SVD processing of the kernel image.

In other embodiments, the set of separable kernels are predetermined for a given non-separable kernel image. The horizontal and vertical kernel data may also be pre-calculated.

In act 26, the camera data is adjusted for compatibility with the parallel application of the SVD kernel data. The adjustment may be implemented at any time before the parallel processing of the disclosed embodiments is initiated. In some embodiments, the camera data may be adjusted to include a number of rows and/or columns to be compatible with the parallel application of the SVD kernel data. For example, the number of rows and columns may be adjusted to be multiples of four so that parallel processing of four rows or columns can be implemented. The adjustment may add or remove rows or columns. In cases where rows or columns are added (e.g., along an edge of the input image), the added camera data may be zero intensity, interpolated values, extrapolated values, or any other intensity level. Any number of zeros may be padded to the camera data. In cases where rows or columns are removed, the removed camera data may be located along an edge of the input image. The resulting dimensions of the camera data are referenced below as $l_1$ and $o_1$.

The act 26 is optional. In some cases, the camera data need not be adjusted, even if not compatible with the parallel processing. For instance, the disclosed methods may parallel process a number of rows and columns of the input image as possible, and then process any remaining rows individually.

In act 28, an amount of space (e.g., a number of buffers) in one or more memories is allocated to facilitate the implementation of the convolution operation. The memory buffers may be used to store the camera data, the SVD kernel data, any intermediate data generated during the parallel processing, and/or final or output data. The allocation of memory space may occur at any time before the initiation of the parallel processing. The memory buffers for the camera data, the SVD kernel data, and other data may be allocated at the same time or at different times.

In one example, a pair of two-dimensional memory buffers is allocated for the input image-related data, such as the camera data, which are referenced below as image buffers $I_1$ and $I_2$. The image buffers may be configured to facilitate single-instruction, multiple-data (SIMD) or other parallel processing. For example, the image buffers may be byte aligned buffers, such as 16 byte aligned buffers with $l_1$ rows and $o_1$ columns to handle the processing of the camera data. The 16 byte alignment may be used to support Intel Streaming SIMD Extension (SSE) or other parallel processing during the convolution operation. Other ways in which the addresses of the memory buffers or memory space correspond with the size of the floating point values may be used.

The memory buffer allocation may also include allocating a pair of memory buffers to hold the SVD kernel data. In this example, the pair of memory buffers is configured to hold the horizontal and vertical kernel data, respectively. For example, the horizontal and vertical kernel memory buffers may be one-dimensional memory buffer with dimensions $4m$ and $4n$, respectively, to hold the horizontal and vertical kernel data. The horizontal and vertical kernel memory buffers are referenced below as $B_h$ and $B_v$, respectively. The kernel memory buffers may also be byte aligned (e.g., 16 byte aligned) to support the parallel processing (e.g., SSE or other SIMD processing).

Another one-dimensional memory buffer may also be allocated at this time to support the convolution operation calculations. The convolution memory buffer may be byte-aligned (e.g., 16 byte aligned) with the size $4 \times n$ to hold four rows of the input image data or camera data. The size supports the horizontal or row convolution as described below.

Figure 4:
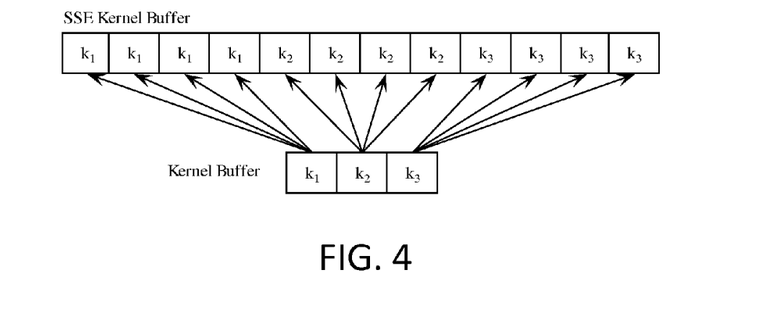
FIG. 4 is a block diagram of an exemplary kernel buffer operation of the image convolution methods of FIGS. 1 and 2 in accordance with one embodiment.

In act 30, the kernel memory buffers $B_h$ and $B_v$ are filled using the values of the horizontal and vertical kernels, $KH_m^i$ and $KV_n^i$, respectively. The kernel memory buffers may be filled with the SVD kernel data in a manner that supports the parallel processing (e.g., SSE or other SIMD processing). The SVD kernel data may be repeated within the kernel memory buffer so that the kernel data may be applied to multiple subsets of the camera data in parallel. An example for SVD kernel data with three elements is shown in FIG. 4. The dimension (i.e., three) of the separable kernel data may vary from the example shown in accordance with the dimension of the non-separable kernel image.

The kernel memory buffers may be filled at a different point in the procedure. For example, the kernel memory buffers may be filled upon completion of the SVD processing in the acts 20-24.

In the embodiment of FIG. 2, the generation of the SVD kernel data and/or filling of the kernel memory buffers also includes determining in an act 32 whether to disregard a respective separable kernel of the set of separable kernels. The determination may be based on whether a singular value of the respective kernel is negligible. One of the separable kernels may be disregarded by removing the separable kernel from the convolution operation, thereby reducing the computations. The determination may analyze whether the singular value $\lambda_i$ can be ignored or otherwise removed from the convolution operation via a comparison with, or relative to, the largest singular value $\lambda_{max}$ and/or the resolution or accuracy of the processor or processing system (e.g., for floating point numbers) used to implement the convolution operation.

In one embodiment, the comparison to determine whether SVD kernel data is removed from the processing is based on both the largest singular value $\lambda_{max}$ and/or the floating point number accuracy. For example, a condition for inclusion of the SVD kernel data may be specified as follows:

$$|\lambda_i| \leq 0.5\sqrt{m+n+1}|\lambda_{max}|\epsilon$$

where m and n are the kernel dimensions, $\lambda_{max}$ is the singular value with the largest absolute value, and $\epsilon$ is the difference between 1 and the smallest value greater than 1 that is representable for the floating number data type. Any separable kernel for which the condition is satisfied may be ignored or otherwise removed from the convolution operation.

Figure 5:
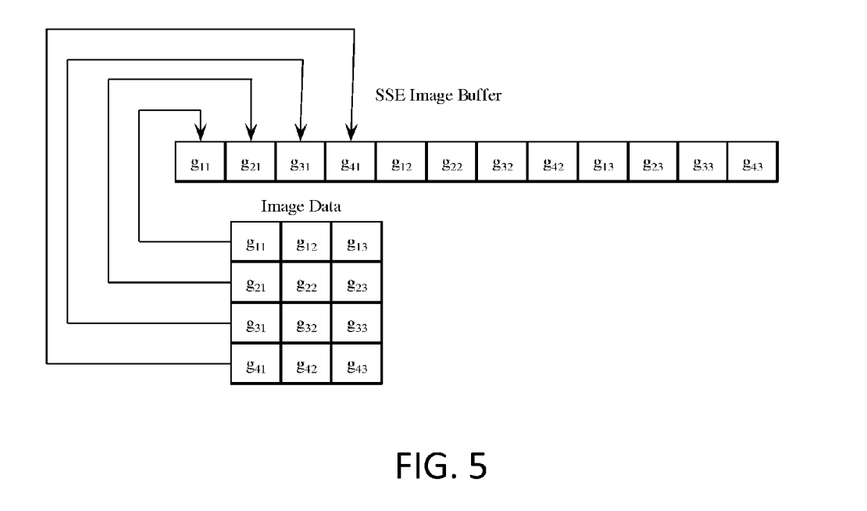
FIG. 5 is a block diagram of an exemplary image buffer operation of the image convolution methods of FIGS. 1 and 2 in accordance with one embodiment.

In preparation for the convolution operation, the convolution buffer may be filled with the camera data in act 34. In some embodiments (e.g., those implementing SSE and other SIMD parallel processing), multiple rows (e.g., four rows) of the input image data or camera data are stored in the convolution buffer. One example of the manner in which the camera data is stored in the convolution buffer is shown in FIG. 5, which depicts four rows of an input image having three columns.

In the embodiment of FIG. 2, convolution of the camera data is implemented in an act 36. In this example, the camera data is convolved with each separable kernel $K_{mn}^i$ whose corresponding singular value $\lambda_i$ cannot be ignored. For each such separable kernel, the convolution operations are applied to the camera data in the convolution buffer containing the four rows of input image data. For example, Intel SSE operations may be used to implement the SIMD parallel processing. Intel SSE operations include intrinsic instructions for addition, subtraction, and multiplication operations in parallel. The separable kernels may then be applied serially, e.g., after finishing the application of one separable kernel to the entire camera image, then another separable kernel is applied.

Each convolution operation instruction (e.g., add, multiply, etc.) is applied to multiple subsets of camera data in parallel. Multiple pixels may thus be processed at the same time. Each subset corresponds with a respective row or a respective column of the camera data. Applying the SVD kernel data in parallel comprises implementing a single-instruction, multiple data (SIMD) operation on multiple rows or multiple columns of the camera data. For example, each SSE instruction is applied to four pixels at the same time.

In the embodiment of FIG. 2, implementing the convolution operation in the act 36 includes an iterative, SIMD application of the horizontal kernel data to a respective number of rows (e.g., four rows) of the camera data to generate row-smoothed data in act 38 (which may include the application of one-dimensional kernels to multiple groups of rows or columns in parallel using multithreading techniques (e.g., OpenMP), storage of the row-smoothed data in an intermediate image buffer in act 40, and application of vertical kernel data to a respective number of columns of row-smoothed data to generate data indicative of individual SVD contributions to the filtered data in act 42. The parallel application of the horizontal and vertical kernel data may be implemented via OpenMP techniques. The SSE or other SIMD processing techniques are used to perform one-dimensional convolution on multiple subsets of the camera data, e.g., four rows of camera data.

In one example, the one-dimensional convolution of the act 38 is concurrently applied to the four rows of camera data in the convolution memory buffer. After the one-dimensional convolution is complete, the row-convolved data (e.g., row-smoothed data) is copied in the act 40 to the two-dimensional image memory buffer I1. The copying may be implemented in a manner that corresponds with the reverse of the memory transfer operation shown in FIG. 5. The vertical one-dimensional convolution may be concurrently applied in act 42 on four columns of the row-convolved camera data stored in the memory buffer I1.

The data indicative of the individual SVD contributions may then be stored in act 44 in an aggregate image buffer (e.g., the memory buffer $I_2$). In some embodiments, such storage of the data indicative of individual SVD contributions is achieved by iteratively accumulating or summing the contributions in an act 46 the data indicative of the individual SVD contributions in the aggregate image buffer. The intrinsic SSE addition operation (or other SIMD operation) may be used to concurrently sum four pixels of the convolved data.

The order in which the acts of FIG. 2 are implemented may vary from the example shown. For example, the memory buffers may be allocated or otherwise assigned or established before the decomposition of the non-separable kernel image.

Some of the acts may be implemented in parallel or otherwise contemporaneously with one or more other acts. Such parallel processing may be provided in addition to the above-described parallel processing involving multiple rows or columns of the camera data. For instance, during the implementation of the convolution operation, one or more multithreading techniques may be used. In one example in which a processing system used to implement the disclosed methods has a dual-core or multi-core CPU, when implementing the horizontal row convolution, a first computing core (or other processor) may be used to compute or convolve the first four rows of the camera data, and a second computing core (or other processor) may be used to compute or convolve the next four rows of the camera data. The vertical convolution computations may be processed in a similar manner. Further or different parallel processing may be incorporated into the disclosed methods if the processing system has a different number of processing cores or other processors.

The OpenMP Application Programming Interface (API) may be used to deploy such multithreading techniques. The OpenMP may be used to implement the multi-threaded processing via a shared memory computing model. Other multithreading techniques may be used, including, for example, GNU techniques.

Figure 3:
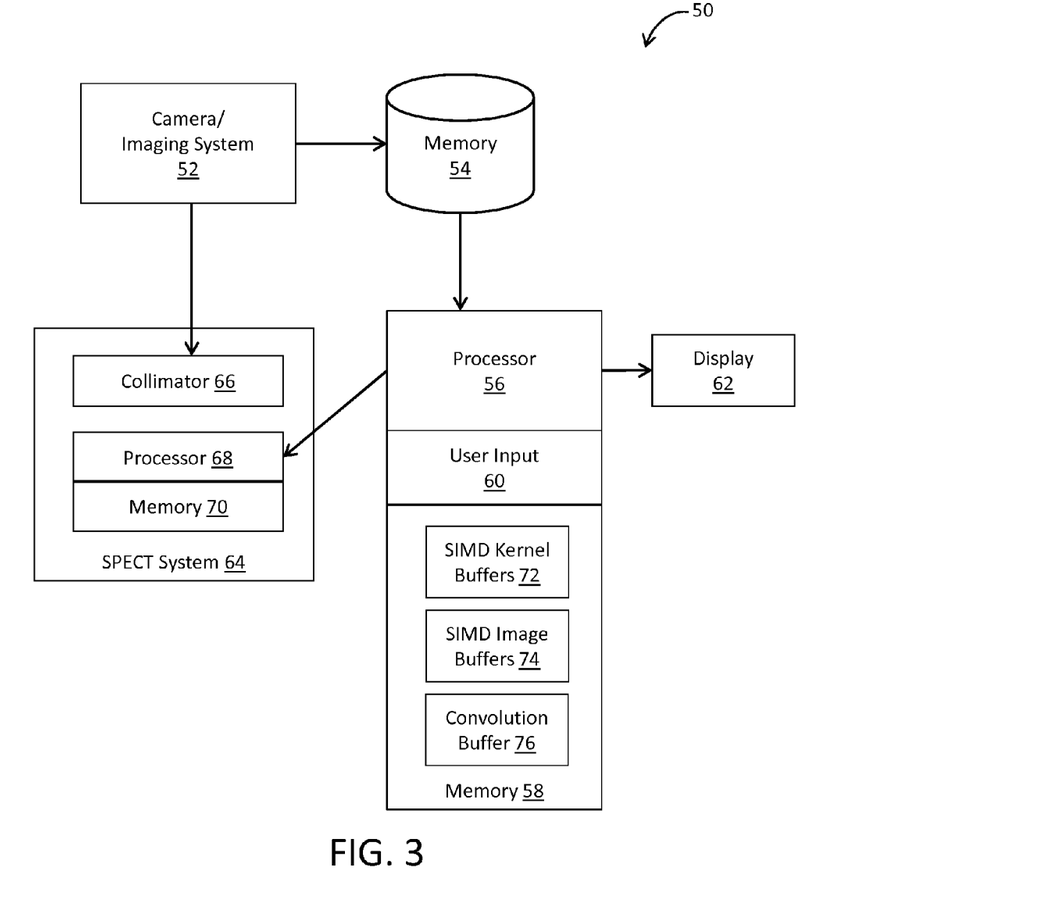
FIG. 3 is a block diagram of one embodiment of an exemplary system for image processing for configuration of an imaging system in accordance with one embodiment.

FIG. 3 depicts an exemplary system 50 configured to facilitate the implementation and/or application of the disclosed convolution operations. In this example, the system 50 includes a camera 52, a memory 54, a processor 56, a memory 58, a user input 60, and a display 62. The system 50 may also include a SPECT system 64 configured via the application of the convolution operations. The system 50 may include additional, fewer, or alternative components. For example, the memories 54 and 58 may be integrated into a single memory.

The camera 52 is configured to generate the camera data. The camera 52 may be any type of imaging system. In some cases, the camera data is generated via projection. The camera 52 may include one or more imaging modalities or scanners. In this example, the camera 52 is configured to capture photographic data representative of a collimator 66 of the SPECT imaging system 64, which may also include a processor 68 and a memory 70. The processor 68 and the memory 70 may be integrated with one or more of the other processor(s) or memory(ies) of the system 50 to any desired extent.

In the embodiment of FIG. 3, the camera data is stored in the memory 54, which may be configured as a database or other data repository. The configuration of the memory 54 may vary. For example, the memory 54 may include any number of memories or data stores. The memory 54 may also be used to store data indicative of one or more non-separable kernels to be applied in the convolution operations. Alternatively or additionally, data indicative of the SVD kernel data generated from such non-separable kernels may be stored in the memory 54.

The SPECT imaging system 64 and the memory 54 may be disposed remotely from one or more other components of the system 50. For example, the SPECT imaging system 64 need not be located at the site of the processor 56. The SPECT imaging system 64 and the memory 54 may be communicatively coupled or connected with the processor 56 via any communication technology, such as a network.

The processor 56 is in communication with one or more of the above-described components of the system 50 to filter (e.g., smooth) the camera data based on the SVD kernel data. The processor 56 may also generate the SVD kernel data. The user input 60 may be used to select a non-separable kernel image or otherwise direct the generation of the SVD kernel data. The processor 56 may also configure the SPECT imaging system 64 based on the results of the convolution operations. The processor 56 may access the camera data stored in the memory 54 or otherwise receive the camera data captured by the camera 52. The processor 56 may be configured to implement one or more image convolution procedures to smooth, filter, or otherwise process the camera data with the kernel data. Once the intensity data is smoothed or otherwise processed, the processor 56 may then generate a representation of the filtered camera data via the display 62. The display 62 is then operable to display the representation during, for instance, a SPECT configuration procedure.

The camera data, the SVD kernel data, and other data may be obtained via any communication technology. Alternatively or additionally, the processor 56 may be integrated with the SPECT system 64 to implement one or more processing tasks of the SPECT system 64 in addition to collimator characterization and/or other configuration tasks.

The processor 56 may be configured to allocate or establish a number of memory buffers in the memory 58 to support the convolution operations. The memory buffers may include one or more intermediate memory buffers to hold one or more subsets of the camera data during processing, as well as one or more aggregate memory buffers to facilitate the accumulation of the results of the convolution operation, as described above. The buffers may be one-dimensional or two-dimensional as described above. In the embodiment of FIG. 2, the memory 58 is configured with one or more kernel data buffers 72, one or more image data buffers 74, and one or more convolution buffers 76. For example, one of the image data buffers may be an intermediate memory buffer, and one of the image data buffers may be an aggregate memory buffer. One or more of the buffers 72, 74, 76 may be configured as byte-aligned buffers or otherwise configured to facilitate SIMD or other parallel processing.

As described above, the processor 56 may be configured to apply horizontal kernel data to respective rows of the camera data to generate row-smoothed data, store the row-smoothed data in one of the image data buffers 74, apply vertical kernel data to respective columns of the row-smoothed data to generate data indicative of individual SVD contributions to the filtered data, and store the data indicative of individual SVD contributions in another one of the image data buffers 74 (e.g., an aggregate image data buffer). The processor 56 may thus accumulate the data indicative of individual SVD contributions in the aggregate image buffer.

The processor 56 (and/or the processor 70) is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 56 is a single device or multiple devices operating in serial, parallel, or separately. The processor 56 may have any number of processing cores distributed over one or more devices. For example, the disclosed methods may be implemented by a pair of central processing units (CPUs) having a total of four processing cores. The processor 56 may be a main processor of a computer, such as a laptop or desktop computer, or may be a processor for handling some tasks in a larger system, such as in an imaging system.

The memory 54 (and/or the memory 58 and/or the memory 70) is a graphics processing memory, video random access memory, random access memory, system memory, cache memory, hard drive, optical media, magnetic media, flash drive, buffer, database, combinations thereof, or other now known or later developed memory device for storing data or video information. The memory 54 is part of an imaging system, part of a computer associated with the processor 56, part of a database, part of another system, or a standalone device.

The acts described in connection with FIGS. 1 and 2 may be implemented via instructions executed by the programmed processor 56. Data representative of the instructions may be stored in the memory 58 or any other memory. The acts may be implemented by one or more processors and one or more memories in addition or alternative to the processor 56 and the memory 58. The instructions may include computer code to direct the processor 56 or other processor(s) to perform the acts described above. Additional, fewer, or different operations or acts may be implemented. For example, the convolution operations may include the decomposition of the non-separable kernel.

The memory 58 or other memory may include a non-transitory computer readable storage medium storing data representing instructions executable by the programmed processor 56. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, and parallel processing, as described above.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Additional, fewer, or different components may be provided. For example, a network or network connection may be provided, such as for networking with a medical imaging network or data archival system. One or more user inputs or other user interfaces may be provided.

The methods, systems, and computer readable media described above may be used to perform a convolution between a collimator image and a smoothing kernel to determine the positioning of the collimator holes. The performance of the disclosed convolution operation is compared to a direct convolution of the image and the smoothing kernel using a moving window written in the C++ programming language. Using the SVD kernel data and Intel SSE-based parallel processing decreases the processing time of the image convolution from over 100 seconds to about 3 seconds. The disclosed convolution operation with separable kernels also exhibits a significant improvement in processing time (e.g., a difference of about an order of magnitude) over a direct convolution using multithreading techniques alone.

In collimator image convolutions, a number of aspects of the disclosed methods and systems may lead to performance improvements beyond those arising from the parallel processing aspects (e.g., SIMD processing with byte-aligned memory buffers). For example, performance may be improved via applying only some of the separable filters generated from the SVD processing of the kernel image. In the above case, only 11 out of a total of 25 separable filters are applied due to the removal of the other separable filters as described above. Performance may alternatively or additionally be improved due to memory (e.g., cache) efficiency improvements arising from SVD processing and/or SIMD processing. The SIMD processing (e.g., Intel SSE processing) may also lead to performance improvements through efficient use of hardware resources. For example, the computations may be efficiently implemented in memories having 128-bit registers.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method of image processing, the method comprising:
receiving camera data representative of an object;
implementing, with a processor, a convolution operation on the camera data to generate filtered data representative of the object, the convolution operation being configured with singular value decomposition (SVD) kernel data; and
storing the filtered data in a memory;
wherein implementing the convolution operation comprises applying the SVD kernel data in parallel to a plurality of subsets of the camera data, wherein
the object comprises a collimator; and
storing the filtered data comprises configuring an imaging system in accordance with the filtered data, the imaging system comprising the collimator.

2. The method of claim 1, further comprising:
decomposing kernel image data into a set of separable kernels; and
generating the SVD kernel data by calculating horizontal and vertical kernel data for the set of separable kernels.

3. The method of claim 2, wherein generating the SVD kernel data comprises determining whether to disregard a respective kernel of the set of separable kernels based on whether a singular value of the respective kernel is negligible.

4. The method of claim 2, wherein implementing the convolution operation further comprises allocating a pair of kernel buffers to hold the horizontal and vertical kernel data, respectively.

5. The method of claim 4, wherein the pair of kernel buffers are configured as byte-aligned buffers.

6. The method of claim 1, wherein:
each subset of the plurality of subsets of the camera data comprises a respective row or a respective column of the camera data; and
applying the SVD kernel data in parallel comprises implementing a single-instruction, multiple data (SIMD) operation on multiple rows or multiple columns of the camera data.

7. The method of claim 6, wherein:
implementing the convolution operation further comprises allocating intermediate and aggregate image buffers; and
the intermediate and aggregate image buffers are configured as byte-aligned buffers.

8. The method of claim 7, wherein implementing the convolution operation further comprises:
applying horizontal kernel data to respective rows of the camera data to generate row-smoothed data;
storing the row-smoothed data in the intermediate image buffer;
applying vertical kernel data to respective columns of the row-smoothed data to generate data indicative of individual SVD contributions to the filtered data; and
storing the data indicative of individual SVD contributions in the aggregate image buffer.

9. The method of claim 8, wherein storing the data indicative of individual SVD contributions comprises accumulating the data indicative of individual SVD contributions in the aggregate image buffer.

10. The method of claim 1, further comprising adjusting the camera data to include a number of rows and columns to be compatible with the parallel application of the SVD kernel data.

11. A non-transitory computer readable storage medium having stored therein data representing instructions executable by a programmed processor for image processing, the instructions comprising computer code to:
receive camera data representative of an object;
apply singular value decomposition (SVD) kernel data to the camera data, the application convolving the camera data with a non-separable kernel represented by the SVD kernel data and generating filtered data representative of the object; and
store the filtered data in a memory;
wherein the instructions to apply the SVD kernel data are configured to apply the SVD kernel data in parallel to multiple rows or multiple columns of the camera data.

12. The computer readable storage medium of claim 11, wherein the instructions to apply the SVD kernel data are configured to apply horizontal kernel data of the SVD kernel data to the multiple rows of the camera data to generate row-filtered camera data and further configured to apply vertical kernel data of the SVD kernel data to multiple columns of the row-filtered camera data.

13. The computer readable storage medium of claim 11, wherein the instructions to apply the SVD kernel data are configured to allocate a pair of byte-aligned buffers to hold the horizontal and vertical kernel data.

14. The computer readable storage medium of claim 11, the instructions comprising further computer code to:
decompose the non-separable kernel into a set of separable kernels; and
generate the SVD kernel data by calculating horizontal and vertical kernel data for the set of separable kernels.

15. The computer readable storage medium of claim 14, wherein the instructions to generate the SVD kernel data are configured to determine whether to disregard a respective kernel of the set of separable kernels based on whether a singular value of the respective kernel is negligible.

16. The computer readable storage medium of claim 11, wherein the instructions to apply the SVD kernel data are configured to implement a single-instruction, multiple data (SIMD) operation on the multiple rows or the multiple columns of the camera data.

17. A system for image processing, the system comprising:
a first memory in which camera data representative of an object is stored;
a processor configured to implement a convolution operation on the camera data to generate filtered data representative of the object, the convolution operation being configured with singular value decomposition (SVD) kernel data; and
a second memory in communication with the processor to store the filtered data;
wherein the processor is further configured to apply the SVD kernel data in parallel to a plurality of subsets of the camera data, wherein the processor is further configured to allocate intermediate and aggregate image buffers in a third memory to facilitate implementation of the convolution operation, wherein the intermediate and aggregate image buffers are configured as byte-aligned buffers.

18. The system of claim 17, wherein the processor is further configured to:
apply horizontal kernel data to respective rows of the camera data to generate row-smoothed data;
store the row-smoothed data in the intermediate image buffer;
apply vertical kernel data to respective columns of the row-smoothed data to generate data indicative of individual SVD contributions to the filtered data; and
accumulate the data indicative of individual SVD contributions in the aggregate image buffer.

19. The system of claim 17, further comprising an imaging system, wherein:
the imaging system comprises the second memory and a collimator;
the camera data is representative of the collimator; and
the processor is configured to configure the imaging system via storage of the filtered data in the second memory.

* * * * *